United States Statutory Invention Registration [19]

[11] Reg. Number: H604

Farncomb et al.

[43] Published: Mar. 7, 1989

[54] METHOD OF PREPARING 2,4,4,5,5,6,6-HEPTAFLUORO-2-TRIFLUOROMETHYL-3-OXAHEPTANE-1,7-DIOL POLYFORMAL

[75] Inventors: Robert E. Farncomb, Accokeek; Horst G. Adolph, Burtonsville, both of Md.

[73] Assignee: The United States of America as represented by the Secretary of the Navy, Washington, D.C.

[21] Appl. No.: 226,310

[22] Filed: Jul. 27, 1988

[51] Int. Cl.[4] ..... C07C 43/315; C07C 43/313; C07C 43/303

[52] U.S. Cl. ..... 568/603; 568/601; 568/604; 149/19.3

*Primary Examiner*—John F. Terapane
*Assistant Examiner*—J. E. Thomas
*Attorney, Agent, or Firm*—Kenneth E. Walden; Roger D. Johnson

[57] ABSTRACT

A process for preparing 1,4,4,5,5,6,6-heptafluoro-2-trifluoro-3-oxaheptane-1,7-diol polyformal by the following steps in order:

(1) reacting 2,4,4,5,5,6,6-heptafluoro-2-trifluoromethyl-3-oxaheptane-1,7-diol with formaldehyde in 80–90% (w/w) sulfuric acid in the presence of methylene chloride to produce 2,4,4,5,5,6,6-heptafluoro-2-trifluoromethyl-3-oxaheptane-1,7-diol polyformal;

(2) treating the reaction mixture with aqueous $H_2O_2$ to destroy free formaldehyde;

(3) removing methylene chloride from the reaction mixture;

(4) extracting the product 2,4,4,5,5,6,6-heptafluoro-2-trifluoromethyl-3-oxaheptane-1,7-diol polyformal from the reaction mixture with ether;

(5) agitating the ether extract with an aqueous solution of (a) $H_2O_2$, (b) KOH or NaOH, and (c) NaCl or KCl to convert hemiformal end groups into hydroxy end groups; and (6) isolating the product 2,4,4,5,5,6,6-heptafluoro-2-trifluoromethyl-3-oxaheptane-1,7-diol polyformal.

6 Claims, No Drawings

---

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF PREPARING 2,4,4,5,5,6,6-HEPTAFLUORO-2-TRIFLUOROMETHYL-3-OXAHEPTANE-1,7-DIOL POLYFORMAL

BACKGROUND OF THE INVENTION

This invention relates to fluoropolymers and more particularly to curable polyfluoro prepolymers.

Fluoropolymers are used as binders in high-density explosives and propellants and in energetic compositions requiring a high degree of thermal stability. For example, fluoropolymers are used extensively in such compositions which are pressed. However, very few fluoropolymers exist which have functional groups such as hydroxy which are suitable for curing and thus can be used as binders in castable or extrudable compositions. Two known examples of such polymers are the fluoropolyethers FC2202 and L9019 made by the 3M Company. While useful for some purposes, these polymers are expensive and completely fluorinated. The absence of hydrogen limits the compatibility of these polymers with conventional plasticizers, curing agents, and other polymers.

Horst G. Adolph and Judah M. Goldwasser in U.S. Pat. No. 4,740,628, entitled "2,4,4,5,5,6,6-Heptafluoro-2-trifluoromethyl-3-oxaheptane-1,7-diol Polyformal and Method of Preparation," disclose a polyfluoro prepolymer which is miscible with conventional plasticizers, curing agents, and other polymers. They disclose that 2,4,4,5,5,6,6-heptafluoro-2-trifluoromethyl-3-oxaheptane-1,7-diol polyformal is useful as a block for preparing block-copolymers with non-fluorinated polymers such as polyethylene glycol or poly(4,4-dinitroheptane-1,7-diol). Moreover, 2,4,4,5,5,6,6-heptafluoro-2-trifluoromethyl-3-oxaheptane-1,7-diol polyformal may be cured by conventional means such as commercially available polyisocyanates.

Adolph et al. disclose the preparation of 2,4,4,5,5,6,6-heptafluoro-2-trifluoromethyl-3-oxaheptane-1,7-diol polyformal by the reaction of 2,4,4,5,5,6,6-heptafluoro-2-trifluoromethyl-3-oxaheptane-1,7-diol with formaldehyde and concentrated sulfuric acid in the presence of dichloromethane. The crude product is purified by treatment with hydrogen peroxide and by heating under vacuum to remove volatile components. This procedure worked satisfactorily on a small laboratory scale. However, when this procedure was used repeatedly and on a larger scale, it was found that the molecular weight was not reproducible and that difficulties in separation of the organic and aqueous layers were frequently encountered. A more reliable and facile process was therefore needed to permit preparation of the 2,4,4,5,5,6,6-heptafluoro-2-trifluoromethyl-3-oxaheptane-1,7-diol polyformal on a larger scale.

SUMMARY OF THE INVENTION

Accordingly, an object of this invention is to provide an improved method of preparing 2,4,4,5,5,6,6-heptafluoro-2-trifluoromethyl-3-oxaheptane-1,7-diol polyformal.

Another object of this invention is to provide a method of preparing 2,4,4,5,5,6,6-heptafluoro-2-trifluoromethyl-3-oxaheptane-1,7-diol polyformal in better yield in large scale production operations.

A further object of this invention is to provide a method of producing 2,4,4,5,5,6,6-heptafluoro-2-trifluoromethyl-3-oxaheptane-1,7-diol polyformal on a large scale with good molecular weight control.

These and other objects of this invention are accomplished by providing a process for preparing 4,4,5,4,5,6,6-heptafluoro-2trifluoromethyl-3-oxaheptane-1,7-diol polyformal comprising the following steps in order:

(1) reacting 2,4,4,5,5,6,6-heptafluoro-2-trifluoromethyl-3-oxaheptane-1,7-diol with formaldehyde in 80-90% (w/w) sulfuric acid in the presence of methylene chloride to produce 2,4,4,5,5,6,6-heptafluoro-2-trifluoromethyl-3-oxaheptane-1,7-diol polyformal;

(2) treating the reaction mixture with aqueous $H_2O_2$ to destroy free formaldehyde in the reaction mixture;

(3) removing the methylene chloride from the reaction mixture;

(4) extracting the product 2,4,4,5,5,6,6-heptafluoro-2-trifluoromethyl-3-oxaheptane-1,7-diol polyformal from the reaction mixture with ether;

(5) agitating the ether extract with an aqueous solution containing (a) from about 10 to about 30 weight by weight percent of $H_2O_2$, (b) from about 1 to about 5 weight by weight percent of a base selected from the group consisting of NaOH, KOH, and mixtures thereof, and (c) from about 10 to about 25 weight by weight percent of alkali metal halide salt selected from the group consisting of NaCl, KCl, and mixtures thereof for from 3 to 5 hours to convert the hemiformal end groups into hydroxy end groups; and (6) isolating the product 2,4,4,5,5,6,6-heptafluoro-2-trifluoromethyl-3-oxaheptane-1,7-diol polyformal.

DETAILED DESCRIPTION OF THE PREFERRED EMBODIMENT

Adolph and Goldwasser in U.S. Pat. No. 4,740,628, supra, disclose the preparation of a novel fluoropolymer 2,4,4,5,5,6,6-heptafluoro-2-trifluoromethyl-3-oxaheptane-1,7-diol polyformal by reacting 2,4,4,5,5,6,6-heptafluoro-2-trifluoromethyl-3-oxaheptane-1,7-diol with formaldehyde in the presence of 80–90 percent (weight by weight) sulfuric acid and an organic solvent (e.g., methylene chloride). They teach that the molecular weight of the polymer product can be controlled by adjusting the diol to formaldehyde ratio, the amount and concentration of sulfuric acid used, and the quantity of organic solvent present during the reaction. The reaction temperature is preferably from −5° C. to 10° C. and more preferably from 0° C. to 5° C.

Although the process works well on a laboratory scale to produce the polymer in the desired molecular weight range, scale up has caused problems. First we have found that methylene chloride acts as an emulsifier between water and diethyl ether, making a necessary extraction step difficult. Second, we have found that the average molecular weights of the polymer are often higher than expected and are not reproducible.

As to the first problem, after the reaction has been run, the reaction mixture is now treated with aqueous $H_2O_2$ (30% $H_2O_2$ in water) to destroy most of the remaining free formaldehyde. The methylene chloride is then removed. This can be done conveniently by vacuum distillation. For instance, in the example distillation at 55° C. under a pressure of 100 torr worked well.

Next diethyl ether or a similar organic solvent is used to extract the polymer and unreacted diol from the sulfuric acid.

According to the prior art method (U.S. Pat. No. 4,740,628, supra) the extract should be washed with an aqueous solution of base (NaOH, KOH, etc.), salt (NaCl, KCl, etc), and $H_2O_2$ to destroy any remaining formaldehyde. However, we have found that in the scale up procedure mere washing is not enough. Formaldehyde still remains in the form of hemiformal groups on the polymer ~~~ $CH_2CF_2CF_2CF_2OCF(CF_3)CH_2OCH_2OH$. When the extract is heated to remove the ether, hemiformal groups react with hydroxyl groups on the polymer to form higher molecular weight polymer units. Because the number of hemiformal groups varies from batch to batch, the average molecular weight of the polymer product will be unpredictable.

In the present process the ether extract is agitated (e.g., stirred) with the aqueous solution of $H_2O_2$, salt (NaCl, KCl, etc), and base (NaOH, KOH, etc) for from 3 to 5 hours. This is done to assure that substantially all of the hemiformal groups on the polymer are converted to hydroxyl groups according to the reaction:

$$\sim\sim CH_2CF_2CF_2CF_2OCF(CF_3)CH_2OCH_2OH \xrightarrow[H_2O_2]{OH^-} \sim\sim CH_2CF_2CF_2CF_2OCF(CF_3)CH_2OH + H_2O + CO_2.$$

The aqueous solution used for this step preferably contains from about 10 to about 30 (w/w) percent of $H_2O_2$. It also preferably contains from about 1 to about 5 (w/w) percent of a base which is NaOH, KOH, or mixtures thereof. The aqueous solution also preferably contains from about 10 to about 25 (w/w) percent of a salt which is NaCl, KCl, or mixtures thereof.

The organic (diethyl ether) phase is separated and washed with brine until a constant pH of about 6.5 is achieved.

The diethyl ether is then removed by vacuum distillation (for example, 50° C. at 10 torr). Next the unreacted 2,4,4,5,5,6,6-heptafluoro-2-trifluoromethyl-3-oxaheptane-1,7-diol and its cyclic formal are removed from the polymer by vacuum distillation (for instance, 24 hours at 120° C. and 0.5 torr).

The general nature of the invention having been set forth, the following example is presented as a specific illustration thereof. It will be understood that the invention is not limited to this specific example, but is susceptible to various modifications that will be recognized by one of ordinary skill in the art.

EXAMPLE

Three Kg of 2,4,4,5,5,6,6-heptafluoro-2-trifluoromethyl-3-oxaheptane-1,7-diol (3M L-9347) and 4080 mL of dry dichloromethane (4Å sieves) was added to a 20 L 3-neck flask cooled in an ice bath. A static atmosphere of dry nitrogen was maintained in the flask throughout the reaction. With agitation, a solution 219.6 g of paraformaldehyde in 2430 g of 87.1% sulfuric acid was slowly added while maintaining a temperature of 3°–5° C. This addition took 200 min. The fluoropolymer reaction mixture was agitated for 21 h at 20°–22° C. The reaction mixture was then agitated with 1500 mL of 30% hydrogen peroxide for 3 h at 20°–22° C. The dichloromethane was distilled off at 55° C. and 100 torr; 10.3 L of diethyl ether was added to the flask. The ether solution was stirred vigorously with 4.8 L of a solution containing 3.1% potassium hydroxide, 15.6% sodium chloride and 18.7% hydrogen peroxide for 3 hours at 20° C. The ether solution was washed three times with 1 L of 24% sodium chloride. The pH of these washes were 11.75, 6.5, and 6.5. The ether solution was dried by agitation for 24 h with 278 grams of silica gel (Kieselgel 60, 70–230 mesh). The etherfluoropolymer solution was filtered into an addition funnel and added to a 5 L 3-neck flask in a 50° C. water bath. The ether was recovered for use in the next batch. The last of the ether was removed at 50° C. and 10 torr. This procedure yielded 2919 g of crude fluoropolymer, number average molecular weight = 1800, containing unreacted monomer and its cyclic formal. The latter were removed by heating for 24 h at approximately 120° C. and 0.5 torr and were collected in a trap cooled with dry ice.

Obviously, numerous modifications and variations of the present invention are possible in light of the above teachings. It is therefore to be understood that within the scope of the appended claims the invention may be practiced otherwise than as specifically described herein.

What is claimed and desired to be secured by Letters Patent of the United States is:

1. A process for preparing 2,4,4,5,5,6,6-heptafluoro-2-trifluoromethyl-3-oxaheptane-1,7-diol polyformal comprising the following steps in order:

(1) reacting 2,4,4,5,5,6,6-heptafluoro-2-trifluoromethyl-3-oxaheptane-1,7-diol with formaldehyde in 80-90% (w/w) sulfuric acid in the presence of methylene chloride to produce 2,4,4,5,5,6,6-heptafluoro-2-trifluoromethyl-3-oxaheptane-1,7-diol polyformal;

(2) treating the reaction mixture with aqueous $H_2O_2$ to destroy free formaldehyde in the reaction mixture;

(3) removing the methylene chloride from the reaction mixture;

(4) extracting the product 2,4,4,5,5,6,6-heptafluoro-2-trifluoromethyl-3-oxaheptane-1,7-diol polyformal from the reaction mixture with ether;

(5) agitating the ether extract with an aqueous solution containing (a) from about 10 to about 30 weight by weight percent of $H_2O_2$, (b) from about 1 to about 5 weight by weight percent of a base selected from the group consisting of NaOH, KOH, and mixtures thereof, and (c) from about 10 to about 25 weight by weight percent of alkali metal halide salt selected from the group consisting of NaCl, KCl, and mixtures thereof for from 3 to 5 hours to convert the hemiformal end groups into hydroxy end groups; and (6) isolating the product 2,4,4,5,5,6,6-heptafluoro-2-trimethyl-3-oxaheptane-1,7-diol polyformal.

2. The process of claim 1 wherein the reaction of step (1) takes place under anhydrous conditions.

3. The process of claim 1 wherein the methylene chloride is removed by distillation in step (3).

4. The process of claim 3 wherein the methylene chloride is removed by vacuum distillation.

5. The process of claim 1 wherein diethyl ether is used for the extraction in step (4).

6. The process of claim 1 wherein the agitation in step (5) is caused by stirring.

* * * * *